(12) United States Patent
Schaub et al.

(10) Patent No.: US 8,697,834 B2
(45) Date of Patent: Apr. 15, 2014

(54) POLYALKYLENEPOLYAMINES BY HOMOGENEOUSLY CATALYZED ALCOHOL AMINATION

(75) Inventors: Thomas Schaub, Neustadt (DE); Boris Buschhaus, Mannheim (DE); Johann-Peter Melder, Böhl-Iggelheim (DE); Rocco Paciello, Bad Dürkheim (DE); Stephan Hüffer, München (DE); Helmut Witteler, Wachenheim (DE)

(73) Assignee: BASF SE, Ludwigshafen (DE)

( * ) Notice: Subject to any disclaimer, the term of this patent is extended or adjusted under 35 U.S.C. 154(b) by 122 days.

(21) Appl. No.: 13/116,649

(22) Filed: May 26, 2011

(65) Prior Publication Data

US 2011/0294977 A1 Dec. 1, 2011

Related U.S. Application Data

(60) Provisional application No. 61/349,915, filed on May 31, 2010.

(51) Int. Cl.
 *C08G 59/64* (2006.01)
 *C08G 59/68* (2006.01)
 *C08G 59/00* (2006.01)
 *C08G 65/00* (2006.01)

(52) U.S. Cl.
 USPC ............ 528/410; 528/398; 528/400; 528/422

(58) Field of Classification Search
 USPC .................................. 528/398, 400, 422, 410
 See application file for complete search history.

(56) References Cited

U.S. PATENT DOCUMENTS

| 3,708,539 A | 1/1973 | Fenton | |
|---|---|---|---|
| 5,977,293 A | 11/1999 | Steuerle et al. | |
| 7,196,033 B2 * | 3/2007 | Renken et al. | 502/317 |

FOREIGN PATENT DOCUMENTS

| DE | 25 30 042 A1 | 1/1977 |
|---|---|---|
| DE | 195 45 874 A1 | 6/1997 |
| EP | 0 034 480 A2 | 8/1981 |
| EP | 0 239 934 A2 | 10/1987 |

OTHER PUBLICATIONS

Ulrich Steuerle, et al., "Aziridines", Ullmann'S Encyclopedia of Industrial Chemistry, 2007, pp. 1-9.
Yoshihisa Watanabe, et al., "The Ruthenium Catalyzed N-Alkylation and N-Heterocyclization of Aniline Using Alcohols and Aldehydes", Tetrahedron Letters, vol. 22, No. 28, 1981, pp. 2667-2670.
Ken-ichi Fujita, et al., "Cp*Ir Complex Catalyzed Hydrogen Transfer Reactions Directed toward Environmentally Benign Organic Synthesis", Synlett, No. 4, 2005, pp. 560-571.
Annegret Tillack, et al., "Salt-Free Synthesis of Tertiary Amines by Ruthenium-Catalyzed Amination of Alcohols", Eur. J. Org. Chem., 2008, pp. 4745-4750.
Annegret Tillack, et al., "A novel ruthenium-catalyzed amination of primary and secondary alcohols", Tetrahedron Letters, vol. 47, 2006, pp. 8881-8885.
Dirk Hollmann, et al., "A General Ruthenium-Catalyzed Synthesis of Aromatic Amines", Angewandte Chemie Int. Ed., vol. 46, 2007, pp. 8291-8294.
M. Haniti S. A. Hamid, et al., "Ruthenium-Catalyzed N-Alkylation of Amines and Sulfonamides Using Borrowing Hydrogen Methodology", J. Am. Chem. Soc., JACS Articles, vol. 131, No. 5, 2009, pp. 1766-1774.
Chidambaram Gunanathan, et al., "Selective Synthesis of Primary Amines Directly from Alcohols and Ammonia", Angewandte Chemie Int. Ed., vol. 47, 2008, pp. 8661-8664.
U.S. Appl. No. 13/680,625, filed Nov. 19, 2012, Strautmann, et al.
U.S. Appl. No. 13/415,409, filed Mar. 8, 2012, Schaub, et al.
U.S. Appl. No. 13/415,412, filed Mar. 8, 2012, Schaub, et al.
U.S. Appl. No. 13/415,174, filed Mar. 8, 2012, Schaub, et al.
U.S. Appl. No. 13/415,466, filed Mar. 8, 2012, Schaub, et al.
International Search Report issued Aug. 26, 2011, in PCT/EP2011/058758 filed May 27, 2011 with English translation of category of cited documents.

* cited by examiner

*Primary Examiner* — Duc Truong
(74) *Attorney, Agent, or Firm* — Oblon, Spivak, McClelland, Maier & Neustadt, L.L.P.

(57) ABSTRACT

The invention relates to a process for the preparation of polyalkylenepolyamines by catalyzed alcohol amination, in which (i) aliphatic aminoalcohols are reacted with one another or (ii) aliphatic diamines or polyamines are reacted with aliphatic diols or polyols with the elimination of water in the presence of a catalyst.

17 Claims, No Drawings

POLYALKYLENEPOLYAMINES BY HOMOGENEOUSLY CATALYZED ALCOHOL AMINATION

The present invention relates to a process for the preparation of polyalkylenepolyamines by catalytic alcohol amination of alkanolamines or of di- or polyamines with di- or polyols.

Polyethyleneimines are valuable products with a large number of different uses. For example, polyethyleneimines are used: a) as adhesion promoters for printing inks for laminate films; b) as auxiliaries (adhesion) for producing multiply composite films, where not only are different polymer layers compatibilized, but also metal films; c) as adhesion promoters for adhesives, for example in conjunction with polyvinyl alcohol, butyrate and acetate and styrene copolymers, or as cohesion promoter for label adhesives; d) low molecular weight PEI can moreover be used as crosslinkers/hardeners in epoxy resins and polyurethane adhesives; e) as primer in coating applications for improving adhesion on substrates such as glass, wood, plastic and metal; f) for improving wet adhesion in standard emulsion paints and also for improving the instantaneous rain resistance of paints for example for road markings; g) as complexing agent with high binding capacity for heavy metals such as Hg, Pb, Cu, Ni and flocculants in water treatment/water processing; h) as penetration auxiliaries for active metal salt formulations in wood preservation; i) as corrosion inhibitors for iron and nonferrous metals; j) for the immobilization of proteins and enzymes. For these applications, it is also possible to use polyalkylenepolyamines which are not derived from the ethyleneimine.

Polyethyleneimines are currently obtained by the homopolymerization of ethyleneimine. Ethyleneimine is a highly reactive, corrosive and toxic intermediate which can be synthesized in different ways (aziridines, Ulrich Steuerle, Robert Feuerhake; in Ullmann's Encyclopedia of Industrial Chemistry, 2006, Wiley-VCH, Weinheim).

In the β-chloroethylamine process, ethyleneimine is obtained by reacting β-chloroethylamine with NaOH. This process may lead to the undesired polymerization of the β-chloroethylamine by HCl elimination, which must be carefully avoided. Moreover, the use of two equivalents of NaOH and the formation of the coproduct NaCl is disadvantageous.

In the Dow process, the ethyleneimine can be obtained by reacting 1,2-dichloroethane with three equivalents of ammonia. The use of large amounts of ammonia, the formation of the coproduct ammonium chloride, the corrosivity of the reaction mixture and also impurities in the product are disadvantageous.

In the Wencker process, in the first step, 2-aminoethanol is reacted with sulfuric acid to give 2-aminoethyl hydrogensulfate. The ethyleneamine is then obtained from this in the second step by adding two equivalents of NaOH. Here too, the use of sulfuric acid and NaOH and also the formation of the coproduct sodium sulfate are disadvantageous.

During the catalytic dehydrogenation of 2-aminoethanol, the ethyleneimine is obtained by the catalytic dehydrogenation of 2-aminoethanol in the gas phase at 250 to 450° C. Disadvantages of this process are the complex product work-up by distillation, the high energy requirement and also the short catalyst life.

Besides the stated disadvantages of the processes for the preparation of ethyleneimine, the synthesis of polyethyleneimines starting from this starting compound is problematic since the highly reactive, toxic and corrosive ethyleneimine has to be handled. It likewise has to be ensured that no ethyleneimine remains in the products obtained and/or wastewater streams.

For the preparation of polyalkylenepolyamines —[($CH_2$)$_x$N]— with alkylene groups>$C_2$ (x>2) not derived from aziridine, there are no processes analogous to the aziridine route, as a result of which there has hitherto been no cost-effective process for their preparation.

The homogenously catalyzed amination of alcohols is known from the literature for the synthesis of primary, secondary and tertiary amines starting from alcohols and amines, with monomeric products being obtained in all of the described embodiments. U.S. Pat. No. 3,708,539 describes the synthesis of primary, secondary and tertiary amines using a ruthenium-phosphane complex. Y. Watanabe, Y. Tsuji, Y. Ohsugi Tetrahedron Lett. 1981, 28, 2667-2670 reports on the preparation of arylamines by the amination of alcohols with aniline using [Ru(PPh$_3$)$_3$Cl$_2$] as catalyst. EP 0 034 480 A2 discloses the preparation of N-alkyl- or N,N-dialkylamines by the reaction of primary or secondary amines with a primary or secondary alcohol using an iridium, rhodium, ruthenium, osmium, platinum, palladium or rhenium catalyst. EP 0 239 934 A1 describes the synthesis of mono- and diaminated products starting from diols such as ethylene glycol and 1,3-propanediol with secondary amines using ruthenium and iridium phosphane complexes. K. I. Fujita, R. Yamaguchi Synlett, 2005, 4, 560-571 describes the synthesis of secondary amines by the reaction of alcohols with primary amines and also the synthesis of cyclic amines by the reaction of primary amines with diols by ring closure using iridium catalysts. In A. Tillack, D. Hollmann, K. Mevius, D. Michalik, S. Bäehn, M. Beller Eur. J. Org. Chem. 2008, 4745-4750, in A. Tillack, D. Hollmann, D. Michalik, M. Beller Tetrahedron Lett. 2006, 47, 8881-8885, in D. Hollmann, S. Bähn, A. Tillack, M. Beller Angew. Chem. Int. Ed. 2007, 46, 8291-8294 and in M. Haniti, S. A. Hamid, C. L. Allen, G. W. Lamb, A. C. Maxwell, H. C. Maytum, A. J. A. Watson, J. M. J. Williams J. Am. Chem. Soc, 2009, 131, 1766-1774 syntheses of secondary and tertiary amines starting from alcohols and primary or secondary amines using homogeneous ruthenium catalysts are described. The synthesis of primary amines by reacting alcohols with ammonia using a homogeneous ruthenium catalyst is reported in "C. Gunanathan, D. Milstein Angew. Chem. Int. Ed. 2008, 47, 8661-8664".

DE-A 26 24 135 discloses the preparation of polyalkylene polyamines by reacting alkylene diamines with diols in the presence of phosphoric acids, anhydrides, metal salts and esters thereof at temperatures from 250 to 350° C. in liquid phase.

It is an object of the present invention to find a process for the preparation of polyalkylenepolyamines in which no aziridine is used and also no undesired coproducts are formed.

The object is achieved by a process for the preparation of polyalkylenepolyamines by catalyzed alcohol amination, in which (i) aliphatic aminoalcohols are reacted with one another or (ii) aliphatic diamines or polyamines are reacted with aliphatic diols or polyols with the elimination of water in the presence of a catalyst, wherein the catalyst is a transition metal complex catalyst which is present in dissolved form in the reaction medium.

According to the invention, polyalkylenepolyamines are obtained by reacting (i) aliphatic aminoalcohols with one another with the elimination of water or (ii) aliphatic diamines or polyamines with aliphatic diols or polyols with the elimination of water, in each case in the presence of a catalyst. Suitable aliphatic aminoalcohols comprise at least one primary or secondary amino group and at least one OH group. Examples are linear or branched alkanolamines such as monoethanolamine, diethanolamine, 3-aminopropan-1-ol, 2-aminopropan-1-ol, 4-aminobutan-1-ol, 2-aminobutan-1-ol, 3-aminobutan-1-ol, 5-aminopentan-1-ol, 1-aminopentan-2-ol, 6-aminohexan-1-ol, 2-aminohexan-1-ol, 7-aminoheptan-1-ol, 2-aminoheptan-2-ol, 8-aminooctan-1-ol, 2-aminooctan-1-ol, 1-(2-hydroxyethyl)piperazine, 2-(2-aminoethoxy)ethanol, butylethanolamine, propylethanolamine, ethylethanolamine and methylethanolamine.

Suitable aliphatic diamines comprise at least two primary or at least one primary and one secondary or at least two secondary amino groups; they preferably comprise two amino groups. Examples are ethylenediamine, 1,3-propylenediamine, 1,2-propylenediamine, 1,4-butylenediamine, 1,2-butylenediamine, 1,5-diaminopentane, 1,2-diaminopentane 1,6-diaminohexane, 1,2-diaminohexane 1,7-diaminoheptane, 1,2-diaminoheptane, 1,8-diaminooctane, 1,2-diaminooctane, 3,3'-dimethyl-4,4'-diaminodicyclohexylmethane, 4,4'-diaminodicyclohexylmethane, isophoronediamine, 2,2-dimethylpropane-1,3-diamine, 4,7,10-trioxamidecane-1,13-diamine, 4,9-dioxadodecane-1,12-diamine, polyether amines, piperazine, 3-(cyclohexyl-amino)propylamine, 3-(methylamino)propylamine and N,N-bis(3-amino-propyl)methylamine.

Examples of aliphatic diols are ethylene glycol, 1,2-propyleneglycol, 1,3-propyleneglycol, 1,4-butyleneglycol, butane-2,3-diol, neopentyl glycol, 1,2-butylene glycol, 2-methyl-1,3-propanediol, 1,5-pentanediol, 1,2-pentanediol, 1,6-hexanediol, 1,2-hexanediol, 1,7-heptanediol, 1,2-heptanediol 1,8-octanediol, 1,2-octanediol, 2,4-dimethyl-2,5-hexanediol, polyTHF, 1,4-bis(2-hydroxyethyl)piperazine, butyldiethanolamine and methyldiethanolamine.

Preferred polyalkylenepolyamine obtainable according to the invention comprise $C_2$-$C_{10}$-alkylene units, particularly preferably $C_2$-$C_6$-alkylene units. These may be linear or branched; they are preferably linear. Examples are ethylene, 1,3-propylene, 1,4-butylene, 1,5-pentylene, 1,2-pentylene, neopentylene and 1,6-hexylene. Cycloalkylene units are also possible, for example 1,3- and 1,4-cyclohexylene.

It is also possible to use mixtures of aliphatic aminoalcohols or mixtures of alkane diols or mixtures of diaminoalkanes in the respective reactions. The resulting polyalkylenepolyamines can comprise alkylene units of different length.

Polyfunctional aminoalcohols having more than one OH group or more than one primary or secondary amino group can also be reacted with one another. This gives highly branched products. Examples of polyfunctional aminoalcohols are diethanolamine, N-(2-aminoethyl)ethanolamine and diisopropanolamine.

Polyols or mixtures of diols and polyols with diamines can also be reacted. It is also possible to react polyamines or mixtures of diamines and polyamines with diols. It is also possible to react polyols or mixtures of diols and polyols with polyamines or mixtures of diamines and polyamines. This gives highly branched products. Examples of polyols are glycerol, trimethylolpropane, sorbitol, triethanolamine and triisopropanolamine. Examples of polyamines are diethylenetriamine, tris(aminoethyl)amine, 1,3,5-triazacyclohexane, 3-(2-aminoethylamino)propylamine, dipropylenetriamine and N,N'-bis(3-aminopropyl)ethylenediamine.

Preference is given to using diols and diamines in an approximately equimolar amount, for example in a molar ratio of 0.7-1.3:1.

The catalyst preferably comprises at least one element from groups 8, 9 or 10 of the Periodic Table of the Elements. The catalyst is a homogeneous catalyst which is present in the reaction medium in dissolved form. The alcohol amination can be carried out in the presence or absence of an additional solvent. The alcohol amination can be carried out in a single-phase or in a two-phase liquid system at temperatures of generally 20 to 250° C. In the case of two-phase reaction systems, the upper phase consists of a nonpolar solvent, which comprises the majority of the homogeneously dissolved catalyst, and the lower phase consists of the polar starting materials, the polyamines formed and also water.

In one preferred embodiment of the invention, (i) monoethanolamine or (ii) ethylene glycol is reacted with ethylenediamine in the presence of a catalyst to give polyethyleneimine.

The polyethyleneimines are formed according to equation 1 or equation 2. The number of ethyleneimine units n is generally between 3 and 50 000.

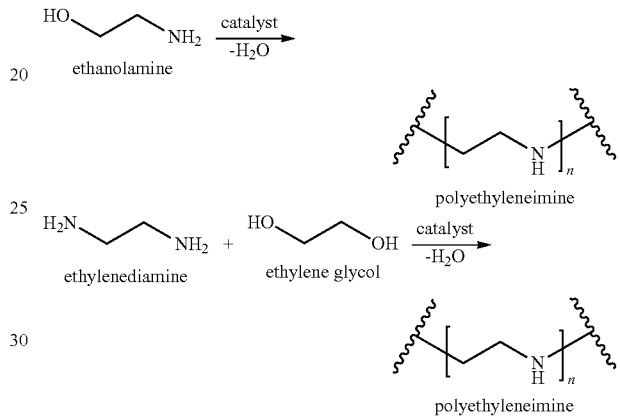

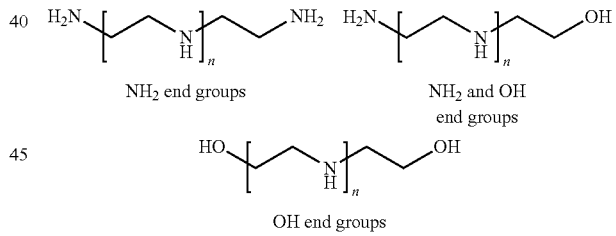

The polyethyleneimines obtained in this way can carry both $NH_2$ groups and also OH groups as end groups on the chain ends.

The number-average molecular weight Mn of the resulting polyethyleneimines is generally from 400 to 2 000 000, preferably from 800 to 750 000 and particularly preferably from 800 to 100 000. The molar mass distribution Mw/Mn is generally in the range from 1.2 to 20, preferably from 1.5-7.5. The cationic charge density (at pH 4-5) is generally in the range from 4 to 22 mequ/g of dry substance, preferably in the range from 6 to 18 mequ/g. Preference is given to forming polyethyleneimines with a high degree of branching (DB). This is determined by 13C-NMR and is defined as follows:

$$DB=D+T/D+T+L$$

where D (dendritic) corresponds to the fraction of tertiary amino groups, L (linear) corresponds to the fraction of secondary amino groups and T (terminal) corresponds to the fraction of primary amino groups.

DB is generally in the range from 0.1-1 and is preferably >0.3.

The polyethyleneimines obtained by the process according to the invention may be present either in linear form or else in branched or polybranched form, and also have ring-shaped structural units.

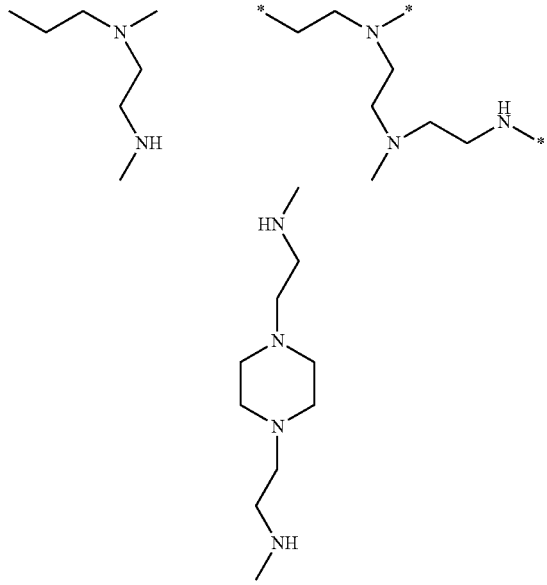

Here, the distribution of the structural units (linear, branched or cyclic) is random. The polyethyleneimines obtained in this way differ from the polyethyleneimines prepared from ethyleneimine by the presence of OH end groups.

In a further embodiment of the invention, a linear alpha, omega-amino alcohol having more than 2 carbon atoms in the alkylene chain is reacted in the presence of a catalyst.

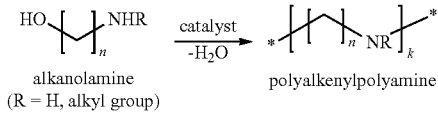

alkanolamine
(R = H, alkyl group)

polyalkenylpolyamine

Preference is given to alkanolamines such as 3-aminopropan-1-ol, 2-aminopropan-1-ol, 4-aminobutan-1-ol, 2-aminobutan-1-ol, 3-aminobutan-1-ol, 5-aminopentan-1-ol, 2-aminopentan-1-ol, 6-aminohexan-1-ol, 2-aminohexan-1-ol, 7-aminoheptan-1-ol, 2-aminoheptan-1-ol, 8-aminooctan-1-ol, 2-aminooctan-1-ol, 1-(2-hydroxyethyl)piperazine and 2-(2-aminoethoxy)ethanol.

Particular preference is given to 3-aminopropan-1-ol and 2-aminopropan-1-ol.

In a further embodiment of the invention, linear alkylenediamines having more than 2 carbon atoms in the alkylene chain are reacted with linear alkane diols having more than 2 carbon atoms in the alkylene chain in the presence of a catalyst.

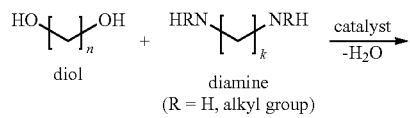

diol diamine
(R = H, alkyl group)

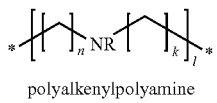

polyalkenylpolyamine

Preferred alkanediols are 1,2-propylene glycol, 1,3-propylene glycol, 1,4-butylene glycol, butane-2,3-diol, neopentyl glycol, 1,2-butylene glycol, 2-methyl-1,3-propanediol, 1,5-pentanediol, 1,2-pentanediol, 1,6-hexanediol, 1,2-hexanediol, 1,7-heptanediol, 1,2-heptanediol, 1,8-octanediol, 1,2-octanediol, 2,4-dimethyl-2,5-hexanediol, polyTHF, 1,4-bis(2-hydroxyethyl)piperazine, butyldiethanolamine and methyldiethanolamine.

Particular preference is given to 2-propylene glycol, 1,3-propylene glycol, 1,4-butylene glycol, 2-methyl-1,3-propanediol, 1,6-hexanediol and neopentyl glycol.

Preferred alkylenediamines are 1,3-propylenediamine, 1,2-propylenediamine, 1,4-butylenediamine, 1,2-butylenediamine, 1,5-diaminopentane, 1,2-diaminopentane, 1,6-diaminohexane, 1,2-diaminohexane, 1,7-diaminoheptane, 1,2-diaminoheptane, 1,8-diaminooctane, 1,2-diaminooctane, 3,3'-dimethyl-4,4'-diaminodicyclohexylmethane, 4,4'-diaminodicyclohexylmethane, isophoronediamine, 2,2-dimethylpropane-1,3-diamine, 4,7,10-trioxamidecane-1,13-diamine, 4,9-dioxadodecane-1,12-diamine, polyetheramines, piperazine, 3-(cyclohexylamino)propylamine, 3-(methylamino)propylamine and N,N-bis(3-aminopropyl)methylamine.

Particular preference is given to 1,3-propylenediamine, 1,2-propylenediamine, 1,6-diaminohexane and 2,2-dimethylpropane-1,3-diamine.

The catalyst is a transition metal complex catalyst which comprises one or more different metals of subgroups of the Periodic Table of the Elements, preferably at least one element from groups 8, 9 and 10 of the Periodic Table of the Elements, particularly preferably ruthenium or iridium. The specified subgroup metals are present in the form of complex compounds. In general, it is a homogeneous catalyst which is present in dissolved form in the reaction medium. Numerous different ligands are suitable. Suitable ligands present in the transition metal complex compounds are, for example, phosphines substituted with alkyl or aryl, polydentate phosphines substituted with alkyl or aryl which are bridged via arylene or alkylene groups, nitrogen-heterocyclic carbenes, cyclopentanedienyl and pentamethylcylopentadienyl, aryl, olefin ligands, hydride, halide, carboxylate, alkoxylate, carbonyl, hydroxide, trialkylamine, dialkylamine, monoalkylamine, nitrogen aromatics such as pyridine or pyrrolidine and polydentate amines. The organometallic complex can comprise one or more different specified ligands.

Preferred ligands are (monodentate) phosphines or (polydentate) polyphosphines, for example diphosphines, with at least one unbranched or branched, acyclic or cyclic, aliphatic, aromatic or araliphatic radical having 1 to 20, preferably 1 to 12 carbon atoms. Examples of branched cycloaliphatic and araliphatic radicals are —$CH_2$—$C_6H_{11}$ and —$CH_2$—$C_6H_5$. Suitable radicals which may be mentioned by way of example are: methyl, ethyl, 1-propyl, 2-propyl, 1-butyl, 2-butyl, 1-(2-methyl)propyl, 2-(2-methyl)propyl, 1-pentyl, 1-hexyl, 1-heptyl, 1-octyl, 1-nonyl, 1-decyl, 1-undecyl, 1-dodecyl, cyclopentenyl, cyclohexyl, cycloheptyl and cyclooctyl, methylcyclopentyl, methylcyclohexyl, 1-(2-methyl)pentyl, 1-(2-ethyl)hexyl, 1-(2-propylheptyl) and norbornyl, phenyl, tolyl and xylyl. The phosphine group can comprise two or three of the specified unbranched or branched acyclic or cyclic, aliphatic, aromatic or araliphatic radicals. These may be identical or different.

In the specified unbranched or branched, acyclic or cyclic, aliphatic, aromatic or araliphatic radicals, individual carbon atoms can also be substituted by further phosphine groups. Also comprised are thus polydentate, for example di- or tridentate, phosphine ligands, the phosphine groups of which are bridged by alkylene or arylene groups. The phosphine groups are preferably bridged by 1,2-phenylene, methylene, 1,2-ethylene, 1,2-dimethyl-1,2-ethylene, 1,3-propylene, 1,4-butylene and 1,5-propylene bridges.

Particularly suitable monodentate phosphine ligands are triphenylphosphine, tritolylphosphine, tri-n-butylphosphine, tri-n-octylphosphine, trimethylphosphine and triethylphosphine.

Particularly suitable polydentate phosphine ligands are bis(diphenylphosphino)methane 1,2-bis(diphenylphosphino)ethane, 1,2-dimethyl-1,2-bis(diphenylphosphino)ethane, 1,2-bis(dicyclohexylphosphino)ethane, 1,2-bis(diethylphosphino)ethane, 1,3-bis(diphenylphosphino)propane, 1,4-bis(diphenylphosphino)butane, 1,5-bis(diphenyl-phosphino)propane and 1,1,1-tris(diphenylphosphinomethyl)ethane.

Particularly suitable ligands which may be mentioned are also cyclopentadienyl and its derivatives mono- to pentasubstituted with alkyl, aryl and/or hydroxy, such as, for example, methylcyclopentadienyl, pentamethylcyclopentadienyl, tetraphenylhydroxycyclopentadienyl and pentaphenylcyclopentadienyl. Further particularly suitable ligands are indenyl and substituted derivatives thereof. Likewise particularly suitable ligands are chloride, hydride and carbonyl. The transition metal complex catalyst can comprise two or more different specified ligands.

The homogeneous catalysts can be used either directly in their active form or else are produced starting from customary standard complexes such as, for example, [Ru(p-cymene)Cl$_2$]$_2$, [Ru(benzene)Cl$_2$]$_n$, [Ru(CO)$_2$Cl$_2$]$_n$, [Ru(CO)$_3$Cl$_2$]$_2$ [Ru(COD)(allyl)], [RuCl$_3$*H$_2$O], [Ru(acetylacetonate)$_3$], [Ru(DMSO)$_4$Cl$_2$], [Ru(PPh$_3$)$_3$(CO)(H)Cl], [Ru(PPh$_3$)$_3$(CO)Cl$_2$], [Ru(PPh$_3$)$_3$(CO)(H)$_2$], [Ru(PPh$_3$)$_3$Cl$_2$], [Ru(cyclopentadienyl)-(PPh$_3$)$_2$Cl], [Ru(cyclopentadienyl)(CO)$_2$Cl], [Ru(cyclopentadienyl)(CO)$_2$H], [Ru(cyclo-pentadienyl)(CO)$_2$]$_2$, [Ru(pentamethylcyclopentadienyl)(CO)$_2$Cl], [Ru(pentamethyl-cyclopentadienyl)(CO)$_2$H], [Ru(pentamethylcyclopentadienyl)(CO)$_2$]$_2$, [Ru(indenyl)-(CO)$_2$Cl], [Ru(indenyl)(CO)$_2$H], [Ru(indenyl)(CO)$_2$]$_2$, ruthenocene, [Ru(binap)Cl$_2$], [Ru(bipyridine)$_2$Cl$_2$*2H$_2$O], [Ru(COD)Cl$_2$]$_2$, [Ru(pentamethylcyclopentadienyl)(COD)Cl], [Ru$_3$(CO)$_{12}$], [Ru(tetraphenylhydroxycyclopentadienyl)(CO)$_2$H], [Ru(PMe$_3$)$_4$(H)$_2$], [Ru(PEt$_3$)$_4$(H)$_2$], [Ru(PnPr$_3$)$_4$(H)$_2$], [Ru(PnBu$_3$)$_4$(H)$_2$]. [Ru(PnOctyl$_3$)$_4$(H)$_2$], [IrCl$_3$*H$_2$O], KIrCl$_4$, K$_3$IrCl$_6$, [Ir(COD)Cl]$_2$, [Ir(cyclooctene)$_2$Cl]$_2$, [Ir(ethene)$_2$Cl]$_2$, [Ir(cyclopentadienyl)-Cl$_2$]$_2$, [Ir(pentamethylcyclopentadienyl)Cl$_2$]$_2$, [Ir(cylopentadienyl)(CO)$_2$], [Ir(penta-methylcyclopentadienyl)(CO)$_2$], [Ir(PPh$_3$)$_2$(CO)(H)], [Ir(PPh$_3$)$_2$(CO)(Cl)], [Ir(PPh$_3$)$_3$(Cl)] with the addition of the corresponding ligands, preferably the aforementioned mono- or polydentate phosphine ligands only under the reaction conditions.

The amount of the metal component in the catalyst, preferably ruthenium or iridium, is generally 0.1 to 5000 ppm by weight, in each case based on the total liquid reaction mixture.

The process according to the invention can be carried out either in a solvent or without solvents.

If the reaction is carried out without solvent, then the homogeneous catalyst is dissolved in the product after the reaction. This can remain in the product or be separated off therefrom by a suitable method. Options for separating off the catalyst are, for example, washing out with a solvent that is immiscible with the product and in which the catalyst dissolves better through suitable choice of the ligands than in the product. Optionally, the catalyst is depleted from the product by multistage extraction (alcohol amination). The extractant used is preferably a solvent that is also suitable for the target reaction, such as toluene, benzene, xylenes, alkanes, such as hexanes, heptanes and octanes, and acyclic or cyclic ethers, such as diethyl ether and tetrahydrofuran, which, following concentration, can be used again together with the extracted catalyst for the reaction. It is also possible to remove the catalyst using a suitable absorber material. Separation can also take place by adding water to the product phase if the reaction is carried out in a water-immiscible solvent. If the catalyst dissolves preferentially in the solvent, it can be separated off with the solvent from the aqueous product phase and optionally be reused. This can be effected through choice of suitable ligands. The resulting aqueous polyalkylenepolyamines can be used directly as technical-grade polyalkylenepolyamine solutions.

If the reaction is carried out in a solvent, then this may be miscible with the product and can be separated off after the reaction by distillation. It is also possible to use solvents which have a miscibility gap with the products or the starting materials. Suitable solvents for this which may be mentioned are, for example, toluene, benzene, xylenes, alkanes, such as hexanes, heptanes and octanes, and acyclic or cyclic ethers, such as diethyl ether, tetrahydrofuran and dioxane. Through suitable choice of the phosphine ligands, the catalyst preferably dissolves in the solvent phase.

Under the reaction conditions, the solvent may also be miscible with the starting materials and the product and only after cooling form a second liquid phase which comprises the majority of the catalyst. Solvents which exhibit this property which may be mentioned, are, for example, toluene, benzene, xylenes, alkanes, such as hexanes, heptanes and octanes. The catalyst can then be separated off together with the solvent and be reused. In this variant, the product phase can be admixed with water. The fraction of the catalyst present in the product can then be separated off by means of suitable absorber materials, such as, for example, polyacrylic acid and salts thereof, sulfonated polystyrenes and salts thereof, activated carbons, montmorillonites, bentonites and also zeolites, or else can be left in the product.

In the embodiment of the two-phase reaction procedure, suitable nonpolar solvents are particularly toluene, benzene, xylenes, alkanes, such as hexanes, heptanes and octanes, in combination with lipophilic phosphine ligands over the transition metal catalyst such as triphenylphosphine, tritolylphosphine, tri-n-butylphosphine, tri-n-octylphosphine, trimethylphosphine, triethylphosphine, bis(diphenylphosphino)methane, 1,2-bis(diphenylphosphino)ethane, 1,2-dimethyl-1,2-bis(diphenylphosphino)-ethane, 1,2-bis(dicyclohexylphosphino)ethane, 1,2-bis(diethylphosphino)ethane, 1,3-bis(diphenylphosphino)propane, 1,4-bis(diphenylphosphino)butane, 1,5-bis(diphenyl-phosphino)propane and 1,1,1-tris(diphenylphosphinomethyl)ethane, through which the transition metal catalyst is enriched in the nonpolar phase. In the case of this embodiment in which the product and the water of reaction and optionally unreacted starting materials form a second phase enriched with these compounds, the majority of the catalyst can be separated off from the product phase by simple phase separation and be reused.

If volatile secondary products or unreacted starting materials or also the water formed during the reaction or added after the reaction for better extraction are undesired, these can be separated off from the product without problems by distillation.

The reaction takes place in the liquid phase at a temperature of generally 20 to 250° C. Preferably, the temperature is at least 100° C. and preferably at most 200° C. The reaction can be carried out at an overall pressure of 0.1 to 20 MPa absolute, which may be either the intrinsic pressure of the solvent at the reaction temperature or the pressure of a gas such as nitrogen, argon or hydrogen. The average reaction time is generally 15 minutes to 100 hours.

It may also be advantageous to continuously remove the water formed during the reaction from the reaction mixture. The water of reaction can be separated off directly by distillation from the reaction mixture or as azeotrope with the addition of a suitable solvent (entrainer) and using a water separator, or be removed by adding water-withdrawing auxiliaries.

The addition of bases can have a positive effect on the product formation. Suitable bases which may be mentioned here are alkali metal hydroxides, alkaline earth metal hydroxides, alkali metal alcoholates, alkaline earth metal alcoholates, alkali metal carbonates and alkaline earth metal carbonates, of which 0.01 to 100 equivalents can be used based on the metal catalyst used.

The invention also relates to the uses of the polyalkylenepolyamines a) as adhesion promoter for printing inks, b) as auxiliary (adhesion) for producing composite films, c) as cohesion promoter for adhesives, d) as crosslinker/hardener for resins, e) as primer in coatings, f) as wet adhesion promoter in emulsion paints, g) as complexing agent and flocculating agent, h) as penetration auxiliary in wood preservation, i) as corrosion inhibitor, j) as immobilizer of proteins and enzymes.

The invention is illustrated in more detail by the examples below.

EXAMPLES

Example 1

Under inert conditions, 0.19 g (0.2 mmol) of [Ru(PPh$_3$)$_3$(H)$_2$(CO)], 0.07 g (0.64 mmol) of KOtBu, 0.45 g (2.2 mmol) of PnBu$_3$, 2.0 g (32.7 mmol) of ethanolamine and 18 ml of toluene are weighed into a shaken steel autoclave with a 40 ml glass insert. The reactor is then heated to 140° C. under an argon pressure of 25 bar and shaken at this temperature and an argon pressure of 30 bar for 20 h at 700 rpm. After the reaction is complete and cooling, two phases are formed, the lower of the two phases being the product phase. In the lower phase, small amounts of dimers (diethanolamine), trimers (triethanolamine, 1-piperazinethanol, triethylenetetramine) and tetramers (tetraethylenepentamine) can be found, which are determined by gas chromatography. The remainder of the product phase consists of non-GC-passable higher oligomers and polymers of ethanolamine. The average molecular weight of the polymers is determined by gel permeation chromatography according to the method of size exclusion chromatography. The eluent used is hexafluoroisopropanol with 0.05% trifluoroacetic acid potassium salt. The measurement is carried out at 30° C. at a flow rate of 1 ml/min and with 10 µl of sample solution on a polyester copolymer column (8 mm*30 cm) with a differential calorimeter or UV photometer as detector. The weight-average of the polymer obtained is 1580 g/mol with a dispersity (Mw/Mn) of 2.5. This corresponds to an average chain length n (number of ethyleneimine units) of the polymer —(CH$_2$CH$_2$NH)$_n$— of 37.

Example 2

Under inert conditions, 0.19 g (0.2 mmol) of [Ru(PPh$_3$)$_3$(H)$_2$(CO)], 0.07 g (0.64 mmol) of KOtBu, 0.09 g (0.452 mmol) of PnBu$_3$, 2.0 g (32.7 mmol) of ethanolamine and 18 ml of toluene are weighed into a shaken steel autoclave with a 40 ml glass insert. The reactor is then heated to 140° C. under an argon pressure of 25 bar and shaken at this temperature and an argon pressure of 30 bar for 20 h at 700 rpm. After the reaction is complete and cooling, two phases are formed, the lower of the two phases being the product phase. In the lower phase, small amounts of dimers (diethanolamine), trimers (triethanolamine, 1-piperazinethanol, triethylenetetramine) and tetramers (tetraethylenepentamine) can be found, which are determined by gas chromatography. The remainder of the product phase consists of non-GC-passable higher oligomers and polymers of ethanolamine. The average molecular weight of the polymers is determined as described in example 1 by gel permeation chromatography according to the method of size exclusion chromatography. The eluent used is hexafluoroisopropanol with 0.05% trifluoroacetic acid potassium salt. The measurement is carried out at 30° C. at a flow rate of 1 ml/min and with 10 µl of sample solution on a polyester copolymer column (8 mm*30 cm) with a differential calorimeter or UV photometer as detector. The weight-average of the resulting polymer is 1070 g/mol with a dispersity (Mw/Mn) of 2.0. This corresponds to an average chain length n of the polymer —(CH$_2$CH$_2$NH)$_n$— of 25.

Example 3

Under inert conditions, 0.19 g (0.2 mmol) of [Ru(PPh$_3$)$_3$(H)$_2$(CO)], 0.07 g (0.64 mmol) of KOtBu, 2.0 g (32.7 mmol) of ethanolamine and 18 ml of toluene are weighed into a shaken steel autoclave with a 40 ml glass insert. The reactor is then heated to 140° C. under a hydrogen pressure of 25 bar and shaken at this temperature and a hydrogen pressure of 30 bar for 20 h at 700 rpm. After the reaction is complete and cooling, two phases are formed, the lower of the two phases being the product phase (1.66 g yield). 0.2 g of the product phase was taken up for the analysis (GC and GPC) in 0.25 g of water and 0.8 g of dimethylacetamide. In the lower phase, small amounts of dimers (diethanolamine), trimers (triethanolamine, 1-piperazinethanol, triethylenetetramine) and tetramers (tetraethylenepentamine) can be found, which were determined by gas chromatography. The remainder of the product phase consists of non-GC-passable higher oligomers and polymers of ethanolamine. The average molecular weight of the polymers is determined as described in example 1. The weight-average of the polymer obtained is 1660 g/mol with a dispersity (Mw/Mn) of 2.6. This corresponds to an average chain length n of the polymer —(CH$_2$CH$_2$NH)$_n$— of 39.

Example 4

Under inert conditions, 0.19 g (0.2 mmol) of [Ru(PPh$_3$)$_3$(H)$_2$(CO)], 0.07 g (0.64 mmol) of KOtBu, 0.09 g (0.452 mmol) of PnBu$_3$, 2.0 g (32.7 mmol) of ethanolamine and 18 ml of toluene are weighed into a shaken steel autoclave with a 40 ml glass insert. The reactor is then heated to 140° C. under a hydrogen pressure of 25 bar and shaken at this temperature and a hydrogen pressure of 30 bar for 20 h at 700 rpm. After the reaction is complete and cooling, two phases are formed, the lower of the two phases being the product phase (1.72 g yield). 0.2 g of the product phase are taken up for the analysis (GC and GPC) in 0.25 g of water and 0.8 g of dimethylacetamide. In the lower phase, small amounts of dimers (diethanolamine), trimers (triethanolamine, 1-piperazinethanol, triethylenetetramine) and tetramers (tetraethylenepentamine) can be found, which are determined by gas chromatography. The remainder of the product phase consists of non-GC-passable higher oligomers and polymers of ethanolamine. The average molecular weight of the polymers was determined as described in example 1. The weight-average of the polymer obtained is 1120 g/mol with a dispersity (Mw/Mn) of 1.7. This corresponds to an average chain length n of the polymer —$(CH_2CH_2NH)_n$— of 26.

Example 5

Under inert conditions, 0.73 g (1.1 mmol) of $[Ir(COD)Cl]_2$, 1.3 g (3.2 mmol) of bis(diphenylphosphino)ethane, 20 g (61.1 mmol) of ethanolamine and 61 g of toluene are weighed into a 250 ml Hastelloy C autoclave with paddle stirrer. The reaction mixture is stirred in the closed autoclave at 150° C. under the intrinsic pressure of the solvent for 20 h. After the reaction is complete and cooling, two phases are formed, the lower of the two phases being the product phase (19 g yield). 1.0 g of the product phase was taken up for the analysis (GC and GPC) in 1 g of water and 4 g of dimethylacetamide. In the lower phase, small amounts of trimers (triethylenetetramine, 1-piperazinethanol) and tetramers (tetraethylenepentamine, piperazine-1,4-diethanol) can be found, which were determined by gas chromatography. The remainder of the product phase consists of non-GC-passable higher oligomers and polymers of ethanolamine. The average molecular weight of the polymers is determined as described in example 1. The weight-average of the polymer obtained is 1880 g/mol with a dispersity (Mw/Mn) of 2.7. This corresponds to an average chain length n of the polymer —$(CH_2CH_2NH)_n$— of 44.

Example 6

Under inert conditions, 22 mg (0.033 mmol) of $[Ir(COD)Cl]_2$, 39.8 mg (0.1 mmol) of bis(diphenylphosphino)ethane, 600 mg (9.81 mmol) of ethanolamine and 3 g of THF are weighed into a shaken steel autoclave with a 13 ml glass insert. The reactor is then heated to 150° C. under an argon pressure of 45 bar and shaken at this temperature and an argon pressure of 50 bar for 20 h at 700 rpm. After the reaction, a phase is formed which was analyzed without further work-up. Small amounts of dimers (diethanolamine), trimers (triethanolamine, 1-piperazinethanol, triethylenetetramine) and tetramers (tetraethylenepentamine) can be found, which were determined by gas chromatography. The remainder of the product phase consists of non-GC-passable higher oligomers and polymers of ethanolamine. The average molecular weight of the polymers is determined as described in example 1. The weight-average of the polymer obtained is 3210 g/mol with a dispersity (Mw/Mn) of 1.7. This corresponds to an average chain length n of the polymer —$(CH_2CH_2NH)_n$— of 70.

Example 7

Under inert conditions, 31.5 mg (0.033 mmol) of $[Ru(1,2-dimethyl-1,2-bis(diphenylphosphino)ethane)_2(H)_2]$, 305.4 mg (4.9 mmol) of ethylenediamine, 295.7 mg (4.9 mmol) of ethylene glycol and 3 g of THF are weighed into a shaken steel autoclave with a 13 ml glass insert. The reactor is then heated to 150° C. under an argon pressure of 45 bar and shaken at this temperature and an argon pressure of 50 bar for 20 h at 700 rpm. After the reaction, a phase is formed which was analyzed without further work-up. Small amounts of dimers (diethanolamine), trimers (triethanolamine, 1-piperazinethanol, triethylenetetramine) and tetramers (tetraethylenepentamine) can be found, which were determined by gas chromatography. The remainder of the product phase consists of non-GC-passable higher oligomers and polymers of ethanolamine. The average molecular weight of the polymers is determined as described in example 1. The weight-average of the polymer obtained is 1710 g/mol with a dispersity (Mw/Mn) of 2.1. This corresponds to an average chain length n of the polymer —$(CH_2CH_2NH)_n$— of 40.

Example 8

Under inert conditions, 30.3 mg (0.033 mmol) of $[Ru(PPH_3)_3(CO)(H)_2]$, 305.4 mg (4.9 mmol) of ethylenediamine, 295.7 mg (4.9 mmol) of ethylene glycol and 3 g of toluene are weighed into a shaken steel autoclave with a 13 ml glass insert. The reactor is then heated to 150° C. under an argon pressure of 45 bar and shaken at this temperature and an argon pressure of 50 bar for 20 h at 700 rpm. After the reaction, two phases are formed, the lower phase being the product, which is separated off and analyzed without further work-up. In the lower phase, small amounts of dimers (diethanolamine), trimers (triethanolamine, 1-piperazinethanol, triethylenetetramine) and tetramers (tetraethylenepentamine) can be found, which are determined by gas chromatography. The remainder of the product phase consists of non-GC-passable higher oligomers and polymers of ethanolamine. The average molecular weight of the polymers is determined as described in example 1. The weight-average of the polymer obtained is 2080 g/mol with a dispersity (Mw/Mn) of 2.3. This corresponds to an average chain length n of the polymer —$(CH_2CH_2NH)_n$— of 48.

Example 9

Under inert conditions, 0.37 g (0.55 mmol) of $[Ir(COD)Cl]_2$, 0.6 g (0.96 mmol) of 2-tris(diphenylphosphinomethyl)ethane, 0.06 g (0.55 mmol) of potassium tert-butylate, 6.1 g (52.0 mmol) of 1,6-hexamethylenediamine, 4.0 g (52.0 mmol) of 1,3-propanediol and 90 ml of xylene are introduced into a 300 ml glass pressurized reactor with gas-introduction stirrer. The reaction mixture is stirred in the closed autoclave at 160° C. under the autogenous pressure of the solvent for 20 h. After the reaction is complete and cooling, two phases are formed, the lower of the two phases being the product phase. 10 ml of water are added to the reaction mixture and stirred for 5 minutes, giving 15.3 g as solution of the product in water as lower phase. The average molecular weight of the oligomers is determined as described in example 1. The weight-average (RI) of the oligomer obtained is 1820 g/mol with a dispersity (Mw/Mn) of 2.0. This corresponds to an average chain length n of the oligomer —$(CH_2CH_2CH_2CH_2CH_2CH_2NHCH_2CH_2CH_2)_n$— of 12. After the reaction, 89% of the iridium used is found in the xylene phase (determined by ascertaining the iridium content in the upper phase and lower phase by atomic adsorption spectroscopy).

Example 10

Under inert conditions, 0.23 g (0.25 mmol) of $[Ru(PPh_3)_3(CO)(H)_2]$, 0.3 g (0.78 mmol) of 1,2-bis(diphenylphosphino)

ethane, 0.31 g (0.78 mmol) of potassium tert-butylate, 15.0 g (129 mmol) of 1,6-hexamethylenediamine, 9.8 g (129 mmol) of 1,3-propanediol and 80 ml of toluene are introduced into a 300 ml glass pressurized reactor with gas-introduction stirrer. The reaction mixture is stirred in the closed autoclave at 150° C. under the autogenous pressure of the solvent for 24 h. After the reaction is complete and cooling, two phases are formed, the lower of the two phases being the product phase. 20 ml of water are added to the reaction mixture and stirred for 5 minutes, giving 39.3 g of solution of the product in water as lower phase. The average molecular weight of the oligomers is determined as described in example 1. The weight-average (RI) of the oligomer obtained is 1790 g/mol with a dispersity (Mw/Mn) of 2.0. This corresponds to an average chain length n of the oligomer —$(CH_2CH_2CH_2CH_2CH_2CH_2NHCH_2CH_2CH_2)_n$— of 12.

Example 11

Under inert conditions, 0.79 g (0.86 mmol) of $[Ru(PPh_3)_3(CO)(H)_2]$, 0.7 g (3.4 mmol) of tri-n-butylphosphane, 0.7 g (3.4 mmol) of potassium tert-butylate, 15.0 g (143 mmol) of diethanolamine and 75 ml of toluene are introduced into a 300 ml glass pressurized reactor with gas-introduction stirrer. The reaction mixture is stirred in the closed autoclave at 150° C. under the autogenous pressure of the solvent for 24 h. After the reaction is complete and cooling, two phases are formed, the lower of the two phases being the product phase. 20 ml of water are added to the reaction mixture and stirred for 5 minutes, giving 15.9 g of solution of the product in water as lower phase. The average molecular weight of the polymers is determined as described in example 1. The weight-average (RI) of the polymer obtained is 2820 g/mol with a dispersity (Mw/Mn) of 4.2. This corresponds to an average chain length n of the polymer $((CH_2CH_2)_2N)_n$ of 40. After the reaction, 97% of the ruthenium used is found in the toluene phase, determined by ascertaining the ruthenium content of the upper phase and lower phase by atomic adsorption spectroscopy.

Example 12

Under inert conditions, 0.73 g (0.11 mmol) of $[Ir(COD)Cl]_2$, 1.29 g (0.32 mmol) of 1,2-bis(diphenylphosphino)ethane, 10.0 g (164 mmol) of ethanolamine and 70 ml of toluene are introduced into a 250 ml Hastelloy C autoclave with paddle stirrer. The reaction mixture is stirred in the closed autoclave at 150° C. under the autogenous pressure of the solvent for 20 h. After the reaction is complete and cooling, two phases are formed, the lower of the two phases being the product phase. 10 ml of water and 6 ml of N,N-dimethylacetamide are added to the reaction mixture and stirred for 5 minutes, giving 18.8 g of lower phase as solution of the product in water/N,N-dimethylacetamide. The average molecular weight of the polymers is determined as described in example 1. The weight-average (RI) of the polymer obtained is 1410 g/mol with a dispersity (Mw/Mn) of 7.7. This corresponds to an average chain length n of the polymer $(CH_2CH_2NH)_n$ of 33.

Example 13

Under inert conditions, 0.73 g (0.11 mmol) of $[Ir(COD)Cl]_2$, 1.37 g (0.32 mmol) of 1,2-bis(dicyclohexylphosphino)ethane, 10.0 g (164 mmol) of ethanolamine and 70 ml of toluene are introduced into a 250 ml Hastelloy C autoclave with paddle stirrer. The reaction mixture is stirred in the closed autoclave at 160° C. under the autogenous pressure of the solvent for 20 h. After the reaction is complete and cooling, two phases are formed, the lower of the two phases being the product phase. 13 ml of water are added to the reaction mixture and stirred for 5 minutes, giving 17.3 g of lower phase as solution of the product in water. The average molecular weight of the polymers is determined as described in example 1. The weight-average (RI) of the polymer obtained is 5460 g/mol with a dispersity (Mw/Mn) of 7.9. This corresponds to an average chain length n of the polymer $(CH_2CH_2NH)_n$ of 127. After the reaction, 80% of the iridium used are found in the toluene phase, determined by ascertaining the iridium content in the upper phase and lower phase by atomic adsorption spectroscopy.

Example 14

Under inert conditions, 0.25 g (0.27 mmol) of $[Ru(PnBu_3)_4(H)_2]$, 0.3 g (1.5 mmol) of tri-n-butylphosphane, 10.0 g (164 mmol) of ethanolamine and 60 g of toluene are weighed into a 250 ml Hastelloy C autoclave with paddle stirrer. The reaction mixture is stirred in the closed autoclave at 160° C. under the autogenous pressure of the solvent for 20 h. After the reaction is complete and cooling, two phases are formed, the lower of the two phases being the product phase. 10 ml of water are added to the reaction mixture and stirred for 5 minutes, giving a solution of the product in water. The average molecular weight of the polymers is determined as described in example 1. The weight-average (RI) of the polymer obtained is 2000 g/mol with a dispersity (Mw/Mn) of 4.7. This corresponds to an average chain length n of the polymer $(CH_2CH_2NH)_n$ of 47.

Example 15

Under inert conditions, 0.43 g (0.27 mmol) of $[Ru(PnOctyl_3)_4(H)_2]$, 0.6 g (1.6 mmol) of tri-n-octylphosphane, 10.0 g (164 mmol) of ethanolamine, 0.1 g (0.9 mmol) of potassium tert-butylate and 60 g of toluene are weighed into a 250 ml Hastelloy C autoclave with paddle stirrer. The reaction mixture is stirred in the closed autoclave at 160° C. under the autogenous pressure of the solvent for 20 h. After the reaction is complete and cooling, two phases are formed, the lower of the two phases being the product phase. 10 ml of water are added to the reaction mixture and stirred for 5 minutes, giving a solution (18.5 g) of the product in water. After the reaction and adding water, 89.9% of the ruthenium used are found in the toluene phase, determined by ascertaining the ruthenium content of the upper phase and lower phase by atomic adsorption spectroscopy. The lower phase is separated off and the water and also unreacted starting material and volatile constituents are removed on a rotary evaporator at 20 mbar and 100° C., giving 5.0 g (71.8% yield) of the pure product. The average molecular weight of the oligomers is determined as described in example 1. The weight-average (RI) of the oligomer obtained is 427 g/mol with a dispersity (Mw/Mn) of 1.1. This corresponds to an average chain length n of the oligomer $(CH_2CH_2NH)_n$ of 10.

Example 16

Under inert conditions, 0.43 g (0.27 mmol) of $[Ru(PnOctyl_3)_4(H)_2]$, 0.6 g (1.6 mmol) of tri-n-octylphosphane, 10.0 g (164 mmol) of ethanolamine and 60 g of toluene are weighed into a 250 ml Hastelloy C autoclave with paddle stirrer. The reaction mixture is stirred in the closed autoclave at 160° C. under the autogenous pressure of the solvent for 20 h. After the reaction is complete and cooling, two phases are formed, the lower of the two phases being the product phase. 10 ml of water are added to the reaction mixture and stirred for 5 minutes, giving a solution (19.0 g) of the product in water. After the reaction and addition of water, 83.0% of the ruthenium used are found in the toluene phase, determined by ascertaining the ruthenium content of the upper phase and lower phase by atomic adsorption spectroscopy. The lower phase is separated off and the water and also unreacted starting material and volatile constituents are removed on a rotary evaporator at 20 mbar and 100° C., giving 6.4 g (90.6% yield) of the pure product. The average molecular weight of the oligomers is determined as described in example 1. The weight-average (RI) of the oligomer obtained is 442 g/mol with a dispersity (Mw/Mn) of 1.2. This corresponds to an average chain length n of the oligomer $(CH_2CH_2NH)_n$ of 10.

Example 17

Under inert conditions, 0.25 g (0.27 mmol) of [Ru(Pn-Butyl)$_4$(H)$_2$], 0.3 g (1.5 mmol) of tri-n-butylphosphane, 10.0 g (164 mmol) of ethanolamine, 0.1 g (0.9 mmol) of potassium tert-butylate and 60 g of toluene are weighed into a 250 ml Hastelloy C autoclave with paddle stirrer. The reaction mixture is stirred in the closed autoclave at 160° C. under the autogenous pressure of the solvent for 10 h. After the reaction is complete and cooling, two phases are formed, the lower of the two phases being the product phase. 10 ml of water are added to the reaction mixture and stirred for 5 minutes, giving a solution (18.0 g) of the product in water. The lower phase is separated off and the water and also unreacted starting material and volatile constituents are removed on a rotary evaporator at 20 mbar and 100° C., giving 6.0 g (85.0% yield) of the pure product. The average molecular weight of the oligomers is determined as described in example 1. The weight-average (RI) of the oligomer obtained is 424 g/mol with a dispersity (Mw/Mn) of 1.1. This corresponds to an average chain length n of the oligomer $(CH_2CH_2NH)_n$ of 10.

Example 18

Under inert conditions, 0.25 g (0.27 mmol) of [Ru(Pn-Butyl$_3$)$_4$(H)$_2$], 0.3 g (1.5 mmol) of tri-n-butylphosphane, 10.0 g (133 mmol) of 3-amino-1-propanol, 0.1 g (0.9 mmol) of potassium tert-butylate and 60 g of toluene are weighed into a 250 ml Hastelloy C autoclave with paddle stirrer. The reaction mixture is stirred in the closed autoclave at 160° C. under the autogenous pressure of the solvent for 20 h. After the reaction is complete and cooling, two phases are formed, the lower of the two phases being the product phase. 10 ml of water are added to the reaction mixture and stirred for 5 minutes, giving a solution (15.7 g) of the product in water. After the reaction and the addition of water, 94.9% of the ruthenium used are found in the toluene phase, determined by ascertaining the ruthenium content of the upper phase and lower phase by atomic adsorption spectroscopy. The lower phase is separated off and the water and also unreacted starting material and volatile constituents are removed on a rotary evaporator at 20 mbar and 100° C., giving 4.1 g (54.0% yield) of the pure product. The average molecular weight of the oligomers is determined as described in example 1. The weight-average (RI) of the oligomer obtained is 411 g/mol with a dispersity (Mw/Mn) of 1.1. This corresponds to an average chain length n of the oligomer $(CH_2CH_2CH_2NH)_n$ of 7.

Example 19

Under inert conditions, 0.25 g (0.27 mmol) of [Ru(Pn-Butyl$_3$)$_4$(H)$_2$], 0.3 g (1.5 mmol) of tri-n-butylphosphane, 10.0 g (133 mmol) of N-methylethanolamine, 0.1 g (0.9 mmol) of potassium tert-butylate and 60 g of toluene are weighed into a 250 ml Hastelloy C autoclave with paddle stirrer. The reaction mixture is stirred in the closed autoclave at 160° C. under the autogenous pressure of the solvent for 20 h. After the reaction is complete and cooling, two phases are formed, the lower of the two phases being the product phase. 10 ml of water are added to the reaction mixture and stirred for 5 minutes, giving a solution (17.3 g) of the product in water. After the reaction and addition of water, 98.8% of the ruthenium used is found in the toluene phase, determined by ascertaining the ruthenium content of the upper phase and lower phase by atomic adsorption spectroscopy. The lower phase is separated off and the water and also unreacted starting material and volatile constituents are removed on a rotary evaporator at 20 mbar and 100° C., giving 4.7 g (61.9% yield) of the pure product. The average molecular weight of the oligomers is determined as described in example 1. The weight-average (RI) of the oligomer obtained is 312 g/mol with a dispersity (Mw/Mn) of 1.1. This corresponds to an average chain length n of the oligomer $(CH_2CH_2NCH_3)_n$ of 6.

Example 20

Under inert conditions, 0.25 g (0.27 mmol) of [Ru(Pn-Butyl$_3$)$_4$(H)$_2$], 0.3 g (1.5 mmol) of tri-n-butylphosphane, 10.0 g (133 mmol) of isopropanolamine, 0.1 g (0.9 mmol) of potassium tert-butylate and 60 g of toluene are weighed into a 250 ml Hastelloy C autoclave with paddle stirrer. The reaction mixture is stirred in the closed autoclave at 160° C. under the autogenous pressure of the solvent for 20 h. After the reaction is complete and cooling, two phases are formed, the lower phase of the two phases being the product phase. 10 ml of water are added to the reaction mixture and stirred for 5 minutes, giving a solution (17.1 g) of the product in water. After the reaction and addition of water, 98.0% of the ruthenium used is found in the toluene phase, determined by ascertaining the ruthenium content of the upper phase and lower phase by atomic adsorption spectroscopy. The lower phase is separated off and the water and also unreacted starting material and volatile substituents are removed on a rotary evaporator at 20 mbar and 100° C., giving 3.4 g (44.8% yield) of the pure product. The product is a complex oligomer mixture, as was ascertained by $^{13}C$ spectroscopy.

Example 21

Under inert conditions, 0.25 g (0.27 mmol) of [Ru(Pn-Butyl$_3$)$_4$(H)$_2$], 0.3 g (1.5 mmol) of tri-n-butylphosphane, 8.3 g (80 mmol) of 1,2-pentanediol, 4.8 g (80 mmol) of ethylenediamine, 0.1 g (0.9 mmol) of potassium tert-butylate and 60 g of toluene are weighed into a 250 ml Hastelloy C autoclave with paddle stirrer. The reaction mixture is stirred in the closed autoclave at 160° C. under the autogenous pressure of the solvent for 20 h. After the reaction is complete and cooling, two phases are formed, the lower of the two phases being the product phase. 10 ml of water are added to the reaction mixture and stirred for 5 minutes, giving a solution (18.4 g) of the product in water. The lower phase is separated off and the water and also unreacted starting material and volatile constituents are removed on a rotary evaporator at 20 mbar and 100° C., giving 4.9 g (48.5% yield) of the pure product. The average molecular weight of the oligomers is determined as described in example 1. The weight-average (RI) of the oligomer obtained is 334 g/mol with a dispersity (Mw/Mn) of 1.2. This corresponds to an average chain length n of the oligomer (CH₂CH(CH₂CH₂CH₃)NHCH₂CH₂NH)$_n$ of 3.

Example 22

Under inert conditions, 0.25 g (0.27 mmol) of [Ru(Pn-Butyl₃)₄(H)₂], 0.3 g (1.5 mmol) of tri-n-butylphosphane, 5.0 g (80 mmol) of ethylene glycol, 8.2 g (80 mmol) of neopentanediamine, 0.1 g (0.9 mmol) of potassium tert-butylate and 60 g of toluene are weighed into a 250 ml Hastelloy C autoclave. The reaction mixture is stirred in the closed autoclave at 160° C. under the autogenous pressure of the solvent for 20 h. After the reaction is complete and cooling, two phases are formed, the lower of the two phases being the product phase. 10 ml of water are added to the reaction mixture and stirred for 5 minutes, giving a solution (17.7 g) of the product in water. The lower phase is separated off and the water and also unreacted starting material and volatile constituents are removed on a rotary evaporator at 20 mbar and 100° C., giving 4.7 g (46.6% yield) of the pure product. The average molecular weight of the oligomers is determined as described in example 1. The weight-average (RI) of the oligomer obtained is 335 g/mol with a dispersity (Mw/Mn) of 1.1. This corresponds to an average chain length n of the polymer (CH₂C(CH₃)₂CHNHCH₂CH₂NH)$_n$ of 3.

Example 23

Under inert conditions, 0.25 g (0.27 mmol) of [Ru(Pn-Butyl₃)₄(H)₂], 0.3 g (1.5 mmol) of tri-n-butylphosphane, 5.0 g (80 mmol) of ethylene glycol, 5.9 g (80 mmol) of 1,3-diaminopropane, 0.1 g (0.9 mmol) of potassium tert-butylate and 60 g of toluene are weighed into a 250 ml Hastelloy C autoclave. The reaction mixture is stirred in the closed autoclave at 160° C. under the autogenous pressure of the solvent for 20 h. After the reaction is complete and cooling, two phases are formed, the lower of the two phases being the product phase. 10 ml of water are added to the reaction mixture and stirred for 5 minutes, giving a solution (17.9 g) of the product in water. The lower phase is separated off and the water and also unreacted starting material and volatile constituents are removed on a rotary evaporator at 20 mbar and 100° C., giving 5.7 g (72.6% yield) of the pure product. The average molecular weight of the oligomers is determined as described in example 1. The weight-average (RI) of the oligomer obtained is 334 g/mol with a dispersity (Mw/Mn) of 1.1.

Example 24

Under inert conditions, 0.43 g (0.27 mmol) of [Ru(PnOctyl₃)₄(H)₂], 10.0 g (164 mmol) of ethanolamine, 0.1 g (0.9 mmol) of potassium tert-butylate and 60 g of toluene are weighed into a 250 ml Hastelloy C autoclave with paddle stirrer. The reaction mixture is stirred in the closed autoclave at 160° C. under the autogenous pressure of the solvent for 20 h. After the reaction is complete and cooling, two phases are formed, the lower of the two phases being the product phase. 10 ml of water are added to the reaction mixture and stirred for 5 minutes, giving a solution (16.4 g) of the product in water. The lower phase is separated off and the water and also unreacted starting material and volatile constituents are removed on a rotary evaporator at 20 mbar and 100° C., giving 5.1 g (72.2% yield) of the pure product. The average molecular weight of the oligomers is determined as described in example 1. The weight-average (RI) of the oligomer obtained is 425 g/mol with a dispersity (Mw/Mn) of 1.1. This corresponds to an average chain length n of the oligomer (CH₂CH₂NH)$_n$ of 10.

Example 25 a) Under inert conditions, 0.43 g (0.27 mmol) of [Ru(PnOctyl₃)₄(H)₂], 10.0 g (164 mmol) of ethanolamine and 60 g of toluene are weighed into a 250 ml Hastelloy C autoclave with paddle stirrer. The reaction mixture is stirred in the closed autoclave at 160° C. under the autogenous pressure of the solvent for 20 h. After the reaction is complete and cooling, two phases are formed, the lower of the two phases being the product phase. 10 ml of water are added to the reaction mixture and stirred for 5 minutes, giving a solution (17.9 g) of the product in water. After the reaction and addition of water, 57.2% of the ruthenium used is found in the toluene phase, determined by ascertaining the ruthenium content of the upper phase and lower phase by atomic adsorption spectroscopy. The lower phase is separated off and the water and also unreacted starting material and volatile constituents are removed on a rotary evaporator at 20 mbar and 100° C., giving 5.5 g (77.9% yield) of the pure product. The average molecular weight of the oligomers is determined as described in example 1. The weight-average (RI) of the oligomer obtained is 431 g/mol with a dispersity (Mw/Mn) of 1.1. This corresponds to an average chain length n of the oligomer (CH₂CH₂NH)$_n$ of 10.

b) The toluene phase (60 g) from example 25a, which comprises the majority of the ruthenium catalyst after the reaction, and 10 g (164 mmol) of fresh ethanolamine are weighed into a 250 ml Hastelloy C autoclave with paddle stirrer under inert conditions. The reaction mixture is stirred in the closed autoclave at 160° C. under the autogenous pressure of the solvent for 20 h. After the reaction is complete and cooling, two phases are formed, the lower of the two phases being the product phase. 10 ml of water are added to the reaction mixture and stirred for 5 minutes, giving a solution (18.1 g) of the product in water. After the reaction and addition of water, 82.0% of the ruthenium used is found in the toluene phase, determined by ascertaining the ruthenium content of the upper phase and lower phase by atomic adsorption spectroscopy. The lower phase is separated off and the water and also unreacted starting material and volatile constituents are removed on a rotary evaporator at 20 mbar and 100° C., giving 4.7 g (66.6% yield) of the pure product. The average molecular weight of the oligomers is determined as described in example 1. The weight-average (RI) of the oligomer obtained is 405 g/mol with a dispersity (Mw/Mn) of 1.1. This corresponds to an average chain length n of the oligomer (CH₂CH₂NH)$_n$ of 9.

Example 26 a) Under inert conditions, 0.5 g (0.54 mmol) of [Ru(PnOctyl₃)₄(H)₂], 0.6 g (3.0 mmol) of tri-n-butylphosphane, 0.2 g (1.8 mmol) of potassium tert-butylate, 20.0 g (328 mmol) of ethanolamine and 60 g of toluene are weighed into a 250 ml Hastelloy C autoclave with paddle stirrer. The reaction mixture is stirred in the closed autoclave at 160° C. under a hydrogen pressure of 30 bar for 20 h. After the reaction is complete and cooling, two phases are formed, the lower of the two phases being the product phase. 20 ml of water are added to the reaction mixture and stirred for 5 minutes, giving a solution (38.2 g) of the product in water. After the reaction and addition of water, 97.6% of the ruthenium used is found in the toluene phase, determined by ascertaining the ruthenium content of the upper phase and lower phase by atomic adsorption spectroscopy. The lower phase is separated off and the water and also unreacted starting material and volatile constituents are removed on a rotary evaporator at 20 mbar and 100° C., giving 10.4 g (73.6% yield) of the pure product. The average molecular weight of the polymers is determined as described in example 1. The weight-average (RI) of the polymer obtained is 1170 g/mol with a dispersity (Mw/Mn) of 3.3. This corresponds to an average chain length n of the polymer $(CH_2CH_2NH)_n$ of 27.

b) The toluene phase (60 g) from example 25a, which comprises the majority of the ruthenium catalyst after the reaction, and 10 g (164 mmol) of fresh ethanolamine are weighed into a 250 ml Hastelloy C autoclave with paddle stirrer under inert conditions. The reaction mixture is stirred in the closed autoclave at 160° C. under the autogenous pressure of the solvent for 20 h. After the reaction is complete and cooling, two phases are formed, the lower of the two phases being the product phase. 10 ml of water are added to the reaction mixture and stirred for 5 minutes, giving a solution of the product in water. The lower phase is separated off and the water and also unreacted starting material and volatile constituents are removed on a rotary evaporator at 20 mbar and 100° C., giving 6.6 g (93.5% yield) of the pure product. The average molecular weight of the polymers is determined as described in example 1. The weight-average (RI) of the polymer obtained is 2920 g/mol with a dispersity (Mw/Mn) of 4.0. This corresponds to an average chain length n of the polymer $(CH_2CH_2NH)_n$ of 68.

The invention claimed is:

1. A process for the preparation of a polyalkylenepolyamine by catalyzed alcohol amination, wherein
    (i) one or more aliphatic aminoalcohols are reacted with one another or
    (ii) one or more aliphatic diamines or polyamines are reacted with one or more aliphatic diols or polyols
   with the elimination of water in the presence of a catalyst,
      and wherein the catalyst is a transition metal complex catalyst, and the catalyst is present in homogeneously dissolved form in the reaction medium.

2. The process according to claim 1, wherein the catalyst comprises at least one element from groups 8, 9 or 10 of the Periodic System of the Elements.

3. The process according to claim 1, characterized in that the catalyst comprises ruthenium or iridium.

4. The process according to claim 1, wherein the catalyst comprises a monodentate or polydentate phosphine ligand.

5. The process according to claim 4, wherein the catalyst comprises a monodentate phosphine ligand selected from the group consisting of triphenylphosphine, tritolylphosphine, tri-n-butylphosphine, tri-n-octylphosphine, trimethylphosphine and triethylphosphine.

6. The process according to claim 4, wherein the catalyst comprises a polydentate phosphine ligand selected from the group consisting of bis(diphenylphosphino)methane 1,2-bis(diphenylphosphino)ethane, 1,2-dimethyl-1,2-bis(diphenylphosphino)ethane, 1,2-bis(dicyclohexylphosphino)ethane, 1,2-bis(diethylphosphino)ethane, 1,3-bis(diphenylphosphino)propane, 1,4-bis(diphenylphosphino)butane, 1,5-bis(diphenylphosphino)propane and 1,1,1-tris(diphenylphosphinomethyl)ethane.

7. The process according to claim 1, wherein the catalyst comprises a ligand selected from the group consisting of cyclopentadienyl, substituted cyclopentadienyl, indenyl and substituted indenyl.

8. The process according to claim 1, wherein the catalyst comprises a ligand selected from the group consisting of hydroxide, hydride, carbonyl and chloride.

9. The process according to claim 1, wherein the reaction is carried out in the presence of a solvent.

10. The process according to claim 9, wherein the solvent is selected from the group consisting of the group consisting of benzene, toluene, xylenes, alkanes, acyclic and cyclic ethers.

11. The process according to claim 1, wherein (i) monoethanolamine or (ii) ethylene glycol is reacted with ethylenediamine to give polyethyleneimine.

12. The process according to claim 1, in which
    (i) aliphatic aminoalcohols are reacted with one another.

13. The process according to claim 2, in which
    (i) aliphatic aminoalcohols are reacted with one another.

14. The process according to claim 3, in which
    (i) aliphatic aminoalcohols are reacted with one another.

15. The process according to claim 1, in which
    (ii) aliphatic diamines or polyamines are reacted with aliphatic diols or polyols with the elimination of water in the presence of a catalyst.

16. The process according to claim 2, in which
    (ii) aliphatic diamines or polyamines are reacted with aliphatic diols or polyols with the elimination of water in the presence of a catalyst.

17. The process according to claim 3, in which
    (ii) aliphatic diamines or polyamines are reacted with aliphatic diols or polyols with the elimination of water in the presence of a catalyst.

* * * * *